United States Patent [19]

Brittain et al.

[11] Patent Number: 4,581,366

[45] Date of Patent: Apr. 8, 1986

[54] ALDOSE REDUCTASE INHIBITION BY SPIRO INDOLINE DERIVATIVES

[75] Inventors: David R. Brittain, Rochdale; Robin Wood, Stockport, both of United Kingdom

[73] Assignee: Imperial Chemical Industries PLC, London, England

[21] Appl. No.: 591,327

[22] Filed: Mar. 19, 1984

[30] Foreign Application Priority Data

May 5, 1983 [GB] United Kingdom ............... 8312379

[51] Int. Cl.$^4$ .................. A61K 31/415; C07D 487/10
[52] U.S. Cl. .................................. 514/389; 548/101; 548/309; 548/485
[58] Field of Search ................. 548/309, 485, 101; 424/273 R; 514/389

[56] References Cited

U.S. PATENT DOCUMENTS 4,490,381 12/1984 Brittain et al. ................ 548/309 X

FOREIGN PATENT DOCUMENTS 28906 5/1981 European Pat. Off. ........... 548/309

*Primary Examiner*—Richard A. Schwartz
*Attorney, Agent, or Firm*—Cushman, Darby & Cushman

[57] ABSTRACT

The invention concerns 1'-(4-bromo-2-fluorobenzyl)-7'-chloro-spiro[imidazolidine-4,3'-indoline]-2,2',5-trione in racemic or dextrorotatory form; pharmaceutical compositions thereof for use in the treatment or prophylaxis of certain complications of diabetes; and processes for its manufacture.

11 Claims, No Drawings

ALDOSE REDUCTASE INHIBITION BY SPIRO INDOLINE DERIVATIVES

This invention concerns novel indoline derivatives and more particularly a novel 1'-substituted-spiro[imidazolidine-4,3'-indoline]-2,2',5-trione which is a potent inhibitor of the enzyme aldose reductase. The invention also concerns pharmaceutical compositions and processes for the manufacture of the novel compound.

The enzyme aldose reductase is responsible in man and other warm-blooded animals for the catalytic conversion of aldoses, for example, glucose and galactose, to the corresponding alditols for example sorbitol and galactitol respectively. Alditols penetrate cell membranes poorly and, once formed, tend to be removed only by further metabolism. As a consequence, alditols tend to accumulate within cells where they are formed, for example in the lens, peripheral nerve tissue and kidney, causing a rise in internal osmotic pressure which may in turn be sufficient to destroy or impair the function of the cells themselves. In addition, raised alditol levels may result in abnormal levels of their metabolites which may themselves impair or damage cellular function. However, the enzyme aldose reductase has a relatively low substrate affinity, that is, it is only effective in the presence of relatively large concentrations of aldose. Such large concentrations of aldose are present in the clinical conditions of diabetes (excessive glucose) and galactosemia (excessive galactose). As a consequence, inhibitors of the enzyme aldose reductase are useful in the reduction or prevention of the development of those complications of protracted diabetes or galactosemia which may be due in part to the accumulation of sorbitol or galactitol respectively. Such complications are, for example, macular oedema, cataract, retinopathy, nephropathy or impaired neural conduction.

It is known from our earlier work that certain 1'-substituted-spiro[imidazolidine-4,3'-indoline]-2,2',5-triones of the formula Z (set out hereinafter) and wherein Ra is a (1-12C)alkyl radical, a phenyl, naphthylmethyl or cinnamyl radical the aromatic rings of which optionally bear one or two halogeno radicals, or Ra is a benzyl radical optionally bearing one, two or three substituents independently selected from halogeno, trifluoromethyl, (1-4C)alkyl, (1-4C)alkoxy, nitro, cyano and hydroxy radicals; and benzene ring A optionally bears one substituent selected from halogeno, (1-4C)alkyl, (1-4C)alkoxy, nitro and hydroxy radicals, or bears two substituents independently selected from halogeno, (1-4C)alkyl and nitro radicals; or a pharmaceutically acceptable salt thereof; but excluding those compounds wherein Ra is a methyl, ethyl, n-propyl or unsubstituted benzyl radical, and benzene ring A is unsubstituted; possess useful aldose reductase inhibitory properties (European patent application, publication No. 28906A1). We have now discovered that a specific novel compound falling within this generic definition but not hitherto described, and the dextrorotatory optical form thereof as measured at 589 nm wavelength, possess surprisingly potent aldose reductase inhibitory properties, and this is the basis for our invention.

According to the invention there is provided the novel compound 1'-(4-bromo-2-fluorobenzyl)-7'-chloro-spiro[imidazolidine-4,3'-indoline]-2,2',5-trione of the formula I (set out hereinafter) in racemic form, the dextrorotatory form thereof, or a salt of either of such forms.

Particular salts of the novel compound of formula I are, for example, salts which may be of use in the isolation, purification or resolution of the free acidic form of said compound, for example the lithium sodium, potassium, calcium, barium, strontium, aluminium, zinc, iron and silver salts thereof, or salts with optically active forms of organic bases, for example with optically active forms of organic quaternary ammonium hydroxides containing at least one asymmetrically substituted carbon atom, for example with an N,N,N-trialkyl-1-(substituted)alkylammonium hydroxide such as N,N,N-trimethyl-(1-phenylethyl)ammonium hydroxide or N,N,N-trimethyl-(2-hydroxy-1-methyl-2-phenyl)ethylammonium hydroxide.

Other particular salts of the novel compound of formula I encompassed by the invention are, for example pharmaceutically acceptable salts of the free acidic form of said compound, for example salts with bases affording physiologically acceptable cations, for example alkali metal and alkaline earth metal salts (such as sodium, potassium, magnesium and calcium salts), aluminium and ammonium salts, and salts with organic amines (such as, methylamine, dimethylamine, trimethylamine, piperidine, morpholine, piperazine, ethanolamine, triethanolamine, N-methylglucamine and tetramethylammonium hydroxide).

The novel compound of formula I may be manufactured in racemic form using any process known in the art for the production of structurally analogous compounds, for example the processes described in our European patent application, publication No. 28906A1. Such processes are provided as a further feature of the invention and are illustrated by the following presently preferred procedures:

(a) Reacting 1-(4-bromo-2-fluorobenzyl)-7-chloroindoline-2,3-dione with a cyanide salt, and ammonium carbonate or carbamate.

A suitable cyanide salt is, for example an alkali metal cyamide such as sodium or potassium cyanide, or a tetra-alkylammonium cyanide such as tetramethylammonium cyanide.

This process is an example of the Bucherer-Bergs synthesis of imidazolidine-2,4-diones (hydantoins) which is well known in the art (see E Ware in *Chemical Reviews*, 1950, 46, 422–425). The process may therefore proceed through the hydroxynitrile of the formula II and/or the amino-nitrile of the formula III. (The formulae are set out hereinafter). These intermediates are not in general sufficiently stable to be isolated. However, they may be generated transiently in process (a), for example, by reacting the indoline-2,3-dione first with hydrogen cyanide, followed by reaction with ammonium carbonate or carbamate. Similarly, the indoline-2,3-dione may be first reacted with ammonia and hydrogen cyanide, followed by reaction with carbon dioxide, conveniently provided by ammonium carbonate or carbamate.

The process is generally performed in a suitable solvent or diluent, for example in a (1-4C)alkanol such as methanol or ethanol, or in ethylene glycol or diethylene glycol, preferably containing water, and at a temperature in the range, for example 20°-100° C.

The ammonium carbonate or carbamate may if necessary be formed in situ in conventional manner. The preparation of the indoline-2,3-dione is described in the accompanying Examples. (b) Reacting a compound of the formula IV (set out hereinafter) wherein Rb is acyl or tri-[(1–4C)alkyl]silyl with ammonium carbonate or carbamate.

A particular value for Rb when it is acyl is, for example, (1–6C)alkanoyl such as acetyl or propionyl, phenylsulphonyl, toluene-p-sulphonyl, benzoyl or benzyloxycarbonyl.

A particular value for Rb when it is tri[(1–4C)-alkyl]silyl is, for example, trimethylsilyl.

Process (b) is a modification of process (a) hereinbefore and consequently similar reaction conditions may be used. Similarly, the ammonium carbonate or carbamate may be formed in situ if desired.

The starting materials of formula IV may be made by conventional procedures. Thus, those compounds of formula IV wherein Rb is acyl may be conveniently obtained, for example, by reacting 1-(4-bromo-2-fluorobenzyl)-7-chloroindoline-2,3-dione with the appropriate acyl halide (e.g. benzoyl chloride, or benzyl chloroformate) in the presence of sodium or potassium cyanide and sodium or potassium hydroxide, in aqueous methylene chloride at 15°–25° C. Similarly, those compounds of formula IV wherein Rb is tri-[(1–4C)alkyl]silyl may be obtained, for example, by reacting the above mentioned indoline-2,3-dione with a tri-[(1–4C)alkyl]silyl cyanide (e.g. trimethylsilyl cyanide) at 15°–40° C. in a non-aqueous solvent such as 1,2-dimethoxyethane.

The novel intermediate 1-(4-bromo-2-fluorobenzyl)-7-chloroindoline-2,3-dione may be obtained, for example by reaction of the corresponding 1-unsubstituted indoline-2,3-dione with a 4-bromo-2-fluorobenzyl halide (especially the bromide or chloride) in the presence of a suitable base such as potassium hydroxide, potassium carbonate or sodium acetate.

It will be apparent that the above processes produce the compound of formula I in the form of its base-addition salts, which may readily be converted to the free acid form by conventional procedures, for example by treatment with an inorganic acid, such as hydrochloric acid. Other salts of the free acid form of the compound of formula I may be obtained by conventional procedures, for example by reaction with the appropriate base or another salt thereof.

When the dextrorotatory optically active form of the compound of formula I is required, the racemic form of said compound may be reacted with an optically active form of a suitable organic base, for example especially with an N,N,N-trialkyl-(1-phenylethyl)ammonium hydroxide such as N,N,N-trimethyl-(1-phenylethyl)ammonium hydroxide, followed by conventional separation of the diastereoisomeric mixture of salts thus obtained, for example by fractional crystallisation from a suitable solvent, for example a (1–4C)alkanol, (such as methanol or ethanol) 2-methoxyethanol or 1,2-dimethoxyethane, or a mixture thereof, whereafter the dextrorotatory optically active form of the said compound may be liberated by treatment of the appropriate salt with acid using a conventional procedure, for example using an aqueous mineral acid, such as dilute hydrochloric acid.

The property of inhibiting the enzyme aldose reductase in vivo may be demonstrated in the following standard laboratory test. Thus, rats are made diabetic (as evidenced by severe glucosuria being present) by dosing with streptozotocin. The animals are then dosed daily with the test compound for 2–5 days. The animals are then killed 2–4 hours after the final dose and the eye lenses and/or sciatic nerves are removed. After a standard work-up procedure the residual sorbitol levels in each tissue are determined by gas liquid chromatography after conversion to the polytrimethysilyl derivatives. Inhibition of aldose reductase in vivo is then assessed by comparing the residual sorbitol levels in tissues from the dosed diabetic group of rats with those of an undosed group of diabetic rats and an undosed, normal group of rats.

The property of inhibiting the enzyme aldose reductase may also be demonstrated in vitro. Thus, partially purified aldose reductase is isolated in known manner from bovine lenses. The percentage inhibition of this enzyme's ability in vitro to reduce aldoses to polyhydric alcohols, and particularly to reduce glucose to sorbitol, caused by a test compound is then determined using standard spectrophotometric methods.

In the above in vivo test, an effective dose (ED) may be defined as the oral dose at which the residual sorbitol level in the sciatic nerve is reduced to a level similar to that in the sciatic nerve of normal, undosed rats. In this test the novel compound of formula I has an ED of approximately 1.76 mg/kg. as the racemic form and of approximately 0.62 mg/kg. as the dextrorotatory, optically active form. Similarly in the above in vitro test, the novel compound of formula I has an IC50 (concentration necessary to inhibit to the extent of 50% the enzyme's ability to reduce glucose to sorbitol) of approximately $2.4 \times 10^{-8}M$ as the racemic form and of approximately $9.8 \times 10^{-9}M$ as the dextrorotatory, optically active form.

By way of contrast, the preferred group of compounds specifically described at page 6 of our European patent application, publication No. 28906A1 have effective doses (ED) in the range 5–20 mg/kg. in the above in vivo test and IC50 in the range $1.6–3.2 \times 10^{-8}M$ in the above in vitro test.

The compound of formula I will primarily be administered systemically (generally by mouth) to a warm-blooded animal to produce an inhibitory effect on the enzyme aldose reductase, for example at a daily dose of 0.25 to 10 mg./kg. In man it is envisaged that a total daily dose in the range 5 to 250 mg. per man will be administered, given if necessary, in divided doses. The compound of formula I may also be administered topically for a therapeutic or prophylactic effect mediated by inhibition of the enzyme aldose reductase, for example by topical administration direct to the tissue or organ in which inhibition of the enzyme is required, for example by topical administration to the eye. The precise amount of compound administered will necessarily depend on the formulation used. Thus, for example, when a solution is administered a concentration of the compound containing up to 0.001% by weight will generally be used. Similarly, when an ointment is administered a concentration of the compound of up to 2% by weight will generally be used.

The compounds of formula I will normally be administered to warm-blooded animals in the form of special pharmaceutical formulations. The invention therefore also provides a pharmaceutical composition comprising the compound of formula I, or one of its pharmaceutically acceptable salts, together with a pharmaceutically acceptable diluent or carrier.

The compositions may be in a form suitable for oral administration, for example in the form of a tablet, capsule, granule, dispersible powder, syrup, elixir, emulsion, suspension or gel; for parenteral administration, for example in the form of a sterile injectable aqueous suspension or solution, or oily solution or suspension; for rectal administration, for example in the form of a suppository; or for topical administration, for example especially to the eye, in the form of an ointment, gel or sterile solution buffered at an opthalmically acceptable pH, for example in the range pH 7.0–7.6.

Topical formulations may be administered to the eye of an animal, for example man or dogs, requiring treatment for diabetic cataracts or retinopathy in a conventional manner, for example using a drop or eyewash topical formulation.

The compositions may also contain one or more other agents which are known to have a useful effect in the treatment of diabetes or galactosemia, for example a hypoglycaemic agent such as tolbutamide, chlorpropamide, or glybenclamide.

The invention will now be illustrated by the following non-limiting Examples in which, unless otherwise stated:

(i) all evaporations were carried out by rotary evaporation in vacuo:

(ii) all operations were carried out at room temperature, that is in the range 18°–26° C.;

(iii) final products of formula I had satisfactory microanalysis;

(iv) petroleum ether (b.p. 60°–80° C.) is referred to as "petrol 60–80"; and (v) yields are for illustration only and are not necessarily the maximum attainable.

EXAMPLE 1

A stirred suspension of 1-(4-bromo-2-fluorobenzyl)-7-chloro-indoline-2,3-dione (96 g.) in ethanol (1500 ml.) was treated with a solution of potassium cyanide (21.0 g.) and ammonium carbonate (300 g.) in water (1500 ml.). The mixture was stirred at 45°–50° C. for 4 hours. Activated charcoal (50 g.) was added and the mixture was stirred for a further hour at 45°–50° C. The hot mixture was filtered through diatomaceous earth and the filter cake was washed with aqueous ethanol (2×200 ml.; 1:1 v/v) at 60° C. The cooled filtrate was made acid to pH 4 at 0°–5° C. with 10M hydrochloric acid and the precipitated solid was collected by filtration, washed with water and air-dried. Recrystallisation twice from 1:1 v/v ethyl acetate-petrol 60–80 gave (±)-1'-(4-bromo-2-fluorobenzyl)-7'-chloro-spiro[imidazolidine-4,3'-indoline]-2,2',5-trione(60 g.) m.p. 240°–242° C.

The starting material was obtained as follows:

A suspension of 7-chloro-indoline-2,3-dione (15 g.) and potassium carbonate (15 g.) in N,N-dimethylformamide (100 ml.) was stirred and treated with a solution of 4-bromo-2-fluorobenzyl bromide (24.7 g.) in chlorobenzene (100 ml.). The mixture was stirred at 90° C. for five hours; cooled to ambient temperature, and diluted with a mixture of water (500 ml.) and petrol 60–80 (500 ml.). The aqueous phase was adjusted to pH3 with 10M hydrochloric acid. The mixture obtained was separated by filtration. The solid obtained was washed with petrol 60–80, then with water, and recrystallised from ethanol to give 1-(4-bromo-2-fluorobenzyl)-7-chloro-indoline-2,3-dione (15.5 g.), m.p. 164°–166° C.

EXAMPLE 2

(±)-1'-(4-Bromo-2-fluorobenzyl)-7'-chloro-spiro[imidazoline-4,3'-indoline]-2,2',5'-trione (64.4 g.) was dissolved in a 0.253 M solution of (−)-N,N,N-trimethyl-(1-phenylethyl)ammonium hydroxide in methanol (581 ml.). The solution was filtered and the filtrate was evaporated. The residue was dissolved in 2-methoxyethanol (132 ml.). The solution was warmed to 70° C. and then diluted with 1,2-dimethoxyethane (440 ml.) previously warmed to 70° C. The clear solution was stored at 0° C. for 48 hours and the crystals of the quaternary ammonium salt were collected by filtration [27 g.; $[\alpha]_D^{23}$ +21.1°, c. 0.93, MeOH)]. This product was recrystallised from 2-methoxyethanol (55.3 ml.) and 1,2-dimethoxyethane (184 ml.) to give crystals [20 g.; $[\alpha]_D^{23}$ +22° (c.1.11, MeOH)]. A third recrystallisation gave crystals [15.8 g.; $[\alpha]_D^{23}$ +21.9° (c.1.12 MeOH)]. The crystalline salt (15.8 g.) thus obtained was dissolved in methanol (50 ml.) and treated with 0.25 M aqueous hydrochloric acid (105 ml.). The solution was chilled at 0° C. overnight and the solid removed by filtration, washed with water and dried over phosphorus pentoxide under vacuum to give the (+)-enantiomer of 1'-[4-bromo-2-fluorobenzyl]-7'-chloro-spiro[imidazolidine-4,3'-indoline]-2,2',5-trione (9.1 g.), m.p. 260°–262° C., $[\alpha]_D^{23}$ +17.9° (c. 0.89, MeOH).

EXAMPLE 3 (All parts by weight)

A mixture of (+)-1'-(4-bromo-2-fluorobenzyl)-chloro-spiro[imidazolidine-4,3'-indoline]-2,2',5-trione (50 parts), lactose (27 parts) and maize starch (20 parts), was stirred thoroughly and a paste formed from maize starch (2 parts) and water (40 parts) was added and thoroughly mixed in. The resultant mass was passed through a 16 mesh screen, then dried at 60° C. and passed through a 20 mesh screen. Magnesium stearate (1 part) was added to the granules obtained, and the whole compressed by conventional means into tablets, containing 10, 20, 50 or 100 mg. of active ingredient, suitable for oral administration for therapeutic purposes.

EXAMPLE 4

A solution of (+)-1'-(4-bromo-2-fluorobenzyl)-7'-chloro-spiro[imidazolidine-4,3'-indoline]-2,2',5-trione (A) (0.404 g.) in water (25 ml.) and ethanol (5 ml.) containing sodium hydroxide (0.04 g.) was evaporated in vacuo to give the corresponding sodium salt of A as a white solid having a satisfactory microanalysis; found: C,42.5; H,2.3; N,8.7%; $C_{17}H_9BrClFN_3O_3 \cdot H_2O$ requires: C,42.6; H,2.3; N,8.8%.

Chemical Formulae

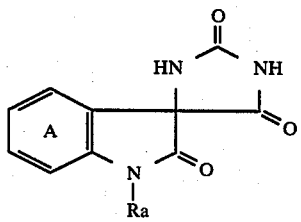

Z

-continued

Chemical Formulae

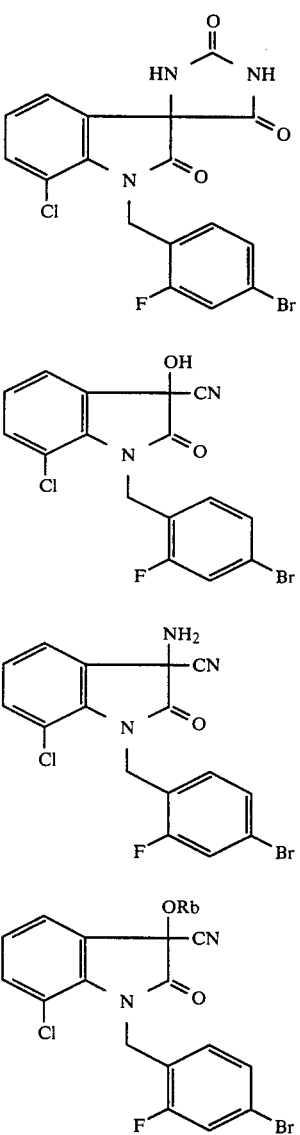

What is claimed is:

1. 1'-(4-Bromo-2-fluorobenzyl)-7'-chloro-spiro[imidazolidine-4,3'-indoline]-2,2',5-trione in racemic or dextrorotatory form, or a salt thereof.

2. The dextrorotatory form of 1'-(4-bromo-2-fluorobenzyl)-7'-chloro-spiro[imidazolidine-4,3'-indoline]-2,2',5-trione, or a salt thereof.

3. A salt as claimed in claim 1 selected from lithium, sodium, potassium, calcium, barium, strontium, aluminium, zinc, iron and silver salts and from salts with optically active forms of organic quaternary ammonium hydroxides.

4. A salt as claimed in claim 1 selected from salts with bases affording physiologically acceptable cations.

5. A salt as claimed in claim 4 selected from alkali metal, alkaline earth metal, aluminium and ammonium salts and from salts with organic amines affording physiologically acceptable cations.

6. A pharmaceutical composition for use in inhibiting the enzyme aldose reductase for therapeutic or prophylactic purposes which comprises an effective amount of 1'-(4-bromo-2-fluorobenzyl)-7'-chloro-spiro[imidazolidine-4,3'-indoline]-2,2'-5-trione in racemic or dextrorotatory form, or a salt thereof with a base affording a physiologically acceptable cation, together with a pharmaceutically acceptable diluent or carrier.

7. A composition as claimed in claim 6 wherein the active ingredient is the dextrorotatory form of 1'-(4-bromo-2-fluorobenzyl)-7'-chloro-spiro[imidazolidine-4,3'-indoline]-2,2',5-trione or a salt thereof with a base affording a physiologically acceptable cation.

8. A composition as claimed in claim 6 in a form suitable for oral, parenteral, rectal or topical administration.

9. A method for the inhibition of the enzyme aldose reductase in a warm-blooded animal requiring such treatment which comprises administering to said animal an effective amount of 1'-(4-bromo-2-fluorobenzyl)-7'-chloro-spiro[imidazoline-4,3'-indoline]-2,2',5-trione in racemic or dextrorotatory form, or of a salt thereof, with a base affording a physiologically acceptable cation.

10. 1-(4-Bromo-2-fluorobenzyl)-7-chloroindoline-2,3-dione.

11. The dextrorotatory quaternary ammonium salt $A^+B^-$ wherein $B^-$ is the anion from the dextrorotatory form of 1'-(4-bromo-2-fluorobenzyl)-7'-chloro-spiro[imidazolidine-4,3'-indoline]-2,2',5-trione and $A^+$ is the cation from the laevorotatory form of N,N,N-trimethyl-(1-phenylethyl)-ammonium hydroxide.

* * * * *